(12) United States Patent
Baba et al.

(10) Patent No.: US 7,110,487 B2
(45) Date of Patent: Sep. 19, 2006

(54) X-RAY MEASURING APPARATUS

(75) Inventors: Rika Baba, Kodaira (JP); Ken Ueda, Ome (JP); Masakazu Okabe, Tsuchiura (JP)

(73) Assignee: Hitachi Medical Corporation, Tokyo (JP)

( * ) Notice: Subject to any disclaimer, the term of this patent is extended or adjusted under 35 U.S.C. 154(b) by 117 days.

(21) Appl. No.: 10/942,892

(22) Filed: Sep. 17, 2004

(65) Prior Publication Data

US 2005/0063507 A1 Mar. 24, 2005

(30) Foreign Application Priority Data

Sep. 19, 2003 (JP) ............... 2003-327473

(51) Int. Cl.
*H05G 1/64* (2006.01)
(52) U.S. Cl. .............. 378/11; 378/19; 378/197
(58) Field of Classification Search .......... 378/11, 378/19, 98.8, 189, 190, 196, 197, 198; 250/370.09
See application file for complete search history.

(56) References Cited

U.S. PATENT DOCUMENTS

| | | | | |
|---|---|---|---|---|
| 4,135,247 A | * | 1/1979 | Gordon et al. | 378/11 |
| 5,493,593 A | | 2/1996 | Müller et al. | 378/4 |
| 6,542,573 B1 | * | 4/2003 | Schomberg | 378/19 |
| 6,546,068 B1 | * | 4/2003 | Shimura | 378/19 |
| 6,868,138 B1 | * | 3/2005 | Clinthorne et al. | 378/98.8 |
| 6,937,697 B1 | * | 8/2005 | Nishide et al. | 378/108 |
| 2004/0013225 A1 | * | 1/2004 | Gregerson et al. | 378/19 |
| 2004/0258195 A1 | * | 12/2004 | Hara | 378/11 |

FOREIGN PATENT DOCUMENTS

| | | | |
|---|---|---|---|
| JP | 8000602 | * | 1/1996 |
| JP | 11-9583 | | 6/1997 |
| JP | 11009583 | * | 1/1999 |

* cited by examiner

*Primary Examiner*—Allen C. Ho
(74) *Attorney, Agent, or Firm*—Reed Smith LLP; Stanley P. Fisher, Esq.; Juan Carlos A. Marquez, Esq.

(57) ABSTRACT

An x-ray measuring apparatus comprises an x-ray source, an x-ray detector, a rotating device, and a processor. The x-ray source generates x-rays to be emitted to a subject. The x-ray detector detects measurement data regarding the subject. The rotating device changes a relative position of the x-ray source and the x-ray detector with respect to the subject. The x-ray detector is shifted by a distance shorter than half the length of the x-ray detector along a line parallel to the plane of rotation, in a tangential direction of the plane of rotation generated by the x-ray source. The processor obtains projection data by executing a logarithmic converting process for the measurement data, multiplies a value of the projection data by a weight, and obtains reconstructed data therefrom.

8 Claims, 6 Drawing Sheets

X-RAY MEASURING APPARATUS

CLAIM OF PRIORITY

The present invention claims priority from Japanese application JP 2003-327473 filed on Sep. 19, 2003, the content of which is hereby incorporated by reference on to this application.

BACKGROUND OF THE INVENTION

The present invention relates to an x-ray measuring technique, and more particularly to an x-ray measuring apparatus which performs tomography on a subject using x-rays.

X-ray measuring apparatuses (hereinafter referred to as CT apparatuses) are used for performing rotation image acquisition during the rotation of an x-ray source and a one-dimensional x-ray detector around the subject, using the one-dimensional x-ray detector. Another type of x-ray measuring apparatuses (hereinafter referred to as cone-beam CT apparatuses) are also used for performing rotation image acquisition during the rotation of an x-ray source and a two-dimensional x-ray detector around the subject, using the two-dimensional x-ray detector. CT apparatuses and cone-beam CT apparatuses are used for performing rotation image acquisition during the rotation of the subject, using a fixed x-ray source and a fixed x-ray detector. These CT apparatuses and cone-beam CT apparatuses are well-know techniques.

In the CT apparatuses and cone-beam CT apparatuses, a set of projection data for three-dimensional reconstructing processing is obtained through correction of a plurality of measurement data acquired by the rotation image acquisition. A three-dimensional image is obtained by three-dimensional reconstructing the obtained projection data, using a three-dimensional reconstruction algorithm. A well-known cone-beam CT reconstruction algorithm includes a Feldkamp method, etc. Such reconstruction algorithms are widely known.

A two-dimensional x-ray detector used in the cone-beam CT may be an I.I.-camera-type x-ray detector or a flat-type x-ray detector, etc. The I.I.-camera-type x-ray detector is a combination of an I.I. (Image Intensifier) and a video camera through an optical system. In the flat-type x-ray detector, sets of an amorphous silicon diode and a TFT are arranged in a square matrix, and these sets and a fluorescent screen are combined in direct. These sensors are well-known techniques.

U.S. Pat. No. 5,493,593 suggests a CT apparatus and a reconstruction process capable of reconstructing a tomographic image in a larger view angle than that of a detector. In this conventional CT apparatus, a one-dimensional detector is displaced in a direction parallel to the plane of rotation generated by an x-ray source and the detector. The detector is placed on one side of a straight line passing through the x-ray source and the rotation center of the x-ray source, and perform photographing. The detector executes a reconstruction process using the one side data of the obtained projection data. In this configuration, non-redundant projection data can be obtained, the photography view is extended along the plane of x-ray source rotation, and the field of view of a reconstructed image can be extended. In this CT apparatus, the extension of the photography view can approximately be double.

Japanese Patent Application Laid-Open No. 11-9583 suggests a cone-beam CP apparatus and a reconstruction process capable of reconstructing a tomographic image in a larger view angle than that of a detector. In this conventional cone-beam CT apparatus, a two-dimensional detector is displaced along the plane of rotation generated by an x-ray source and the detector. The detector is placed on one side of a straight line passing through the x-ray source and the rotation center of the x-ray source, and perform photographing. The obtained projection data is divided in a part corresponding to the axis of rotation of the two-dimensional detector, and a reconstruction process is carried out using one of the divided data. In this configuration, non-redundant projection data can be obtained, the photography view is extended along the plane of x-ray source rotation, and the view of a reconstructed image can be extended. In this cone-beam CT apparatus, the extension of the photography view can approximately be double.

SUMMARY OF THE INVENTION

The above-described conventional apparatuses execute the reconstruction process using only one side of the projection data at a boundary line corresponding to the axis of rotation. The reconstruction process is carried out using the projection data, having both sides discriminated by the center of the axis of rotation. Both sides of the projection data are obtained during the rotations at angles which are 180° different from each other. This causes discontinuity in the projection data, resulting in an artifact produced near the axis of rotation in the reconstructed image.

Such an artifact appears in the form of a concentric circle at the center of the axis of rotation in the tomographic image, and shows a value greater or lower than its surrounding. Near the axis of rotation, the number of projection data pieces contributing to the reconstruction process is less than the number of data pieces in the surrounding. This results in a variation in the projection data due to a variation of the sensitivity of a detecting device or a variation of emitted x-rays, having a definite effect on the reconstructed image. Therefore, a great artifact is easily produced in the axis of rotation, according to the conventional techniques using the "rotation data" which is obtained through rotations at different degrees along the border of the axis of rotation.

It is accordingly an object of the present invention to provide an x-ray measuring technique capable of obtaining a reconstructed image, having a field of view extended along the plane of rotation of an x-ray source without any artifact in its field of view.

In order to attain the above object, the present invention has the features as described below. The below describes the features of typical structures of the present invention.

A first x-ray measuring apparatus of the present invention comprises: an x-ray tube for generating x-rays to be emitted to a subject; an x-ray detector which detects measurement data regarding the subject; a rotating device which changes a relative position of the x-ray tube and the x-ray detector with respect to the subject; and a processor which executes an arithmetic operation for the measurement data, and wherein the x-ray detector is placed and shifted by a distance shorter than half of length of the x-ray detector along a line parallel to plane of rotation, in a tangential direction of the plane of rotation generated by the x-ray tube, and the processor executes a process for obtaining projection data by logarithmic converting the measurement data, a process for multiplying a value of the projection data by a weight, and a process for obtaining reconstructed data by executing a reconstructing process using the data after being multiplied by the weight, thereby obtaining a three-dimensional reconstructed image.

A second x-ray measuring apparatus of this invention comprises: an x-ray tube for generating x-rays to be emitted to a subject; an x-ray detector which detects measurement data regarding the subject; a rotating device which changes a relative position of the x-ray tube and the x-ray detector with respect to the subject; and a processor which executes an arithmetic operation for the measurement data, and wherein the x-ray detector is placed and shifted by a distance shorter than half of length of the x-ray detector along a line parallel to plane of rotation, in a tangential direction of the plane of rotation generated by the x-ray tube, and the processor executes a process for multiplying a value of the measurement data by an exponentially converted value of a weight, a process for obtaining projection data by executing a logarithmic converting process for the data after being multiplied by the weight, and a process for obtaining reconstructed data by executing a reconstructing process using the projection data, thereby obtaining a three-dimensional reconstructed image.

A third x-ray measuring apparatus according to the first or second x-ray measuring apparatus includes the x-ray detector, which is a one-dimensional detector or a two-dimensional detector.

A fourth x-ray measuring according to the third x-ray measuring apparatus executes, in the process for multiplying the weight, sets a rotation center line corresponding to axis of rotation on the measurement data, measures a distance from the rotation center line to an end of the measurement data, sets a boundary line in a position along a longer distance from the rotation center line being equidistant between the position and end of a shorter distance, and sets a weight from the boundary line to an end of the longer distance to 1.0, a weight at the rotation center line to 0.5, and a weight at the end of the shorter distance to 0.0.

In a fifth x-ray measuring apparatus according to the fourth x-ray measuring apparatus, a function expressing the weight is a continuous function in the process for multiplying the weight, and sum of weights in positions which are equidistant apart from the rotation center line is 1.0.

In a sixth x-ray measuring apparatus according to the fifth x-ray measuring apparatus, in the process for multiplying the weight, a differential form of the function representing the weight is a continuous function.

In a seventh x-ray measuring apparatus according to the sixth x-ray measuring apparatus, a profile representing the weight is in a point symmetrical shape with a center about the intersection with the rotation center line.

According to the present invention, there is realized an x-ray measuring apparatus capable of obtaining a reconstructed image in an extended field of view along the plane of rotation without any artifact at the rotation center.

DETAILED DESCRIPTION OF THE PREFERRED EMBODIMENTS

Detailed description of the preferred embodiments will now be made with reference to the drawings.

Figure 2:
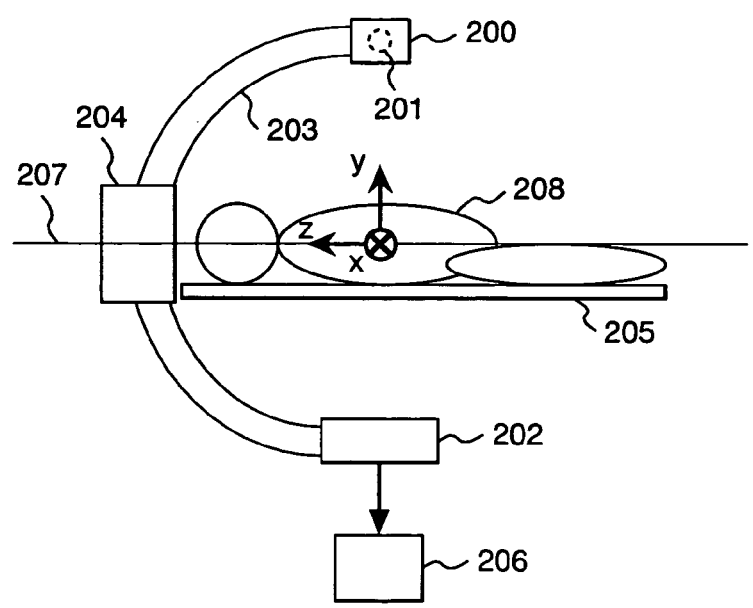
FIG. 2 is a side view exemplarily showing one structure of an x-ray measuring apparatus according to this invention.

FIG. 2 is a side view exemplarily showing one structure of an x-ray measuring apparatus according to this invention. A first x-ray measuring apparatus comprises an x-ray source 201 in an x-ray tube 200, a detector 202, a strut 203, a rotating device 204, a bed 205 and a processor 206. The x-ray source 201 and the detector 202 are installed on the strut 203. The strut 203 may be a C-shaped arm, a U-shaped arm or the like. The strut 203 may be hung from the ceiling or supported on the floor. Under the control of the rotating device 204, the strut 203 rotates axially around a subject 208 lying on the bed 205 about a rotary axis 207. Most commonly, the rotary axis 207 is parallel to the floor, and the plane of rotation is perpendicular to the floor.

Figure 8:
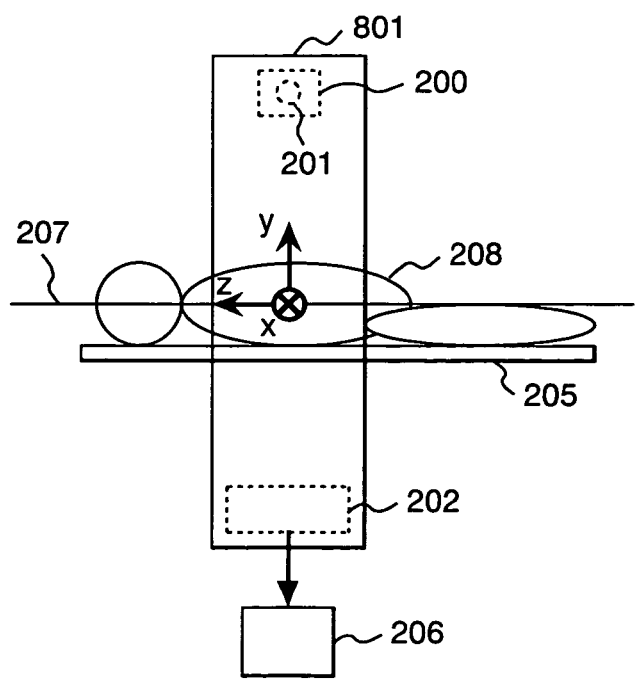
FIG. 8 is a side view exemplarily showing another structure of an x-ray measuring apparatus according of this invention.

FIG. 8 exemplarily shows another structure of an x-ray measuring apparatus according to this invention. A second x-ray measuring apparatus comprises the x-ray source 201 in the x-ray tube 200, the detector 202, a rotary gantry 801, the bed 205 and the processor 206. The x-ray source 201 and the detector 202 are installed on the rotary gantry 801 which rotates around the subject 208 lying on the bed 205. Most commonly, the rotary axis 207 is parallel to the floor, and the plane of rotation is perpendicular to the floor.

Figure 9:
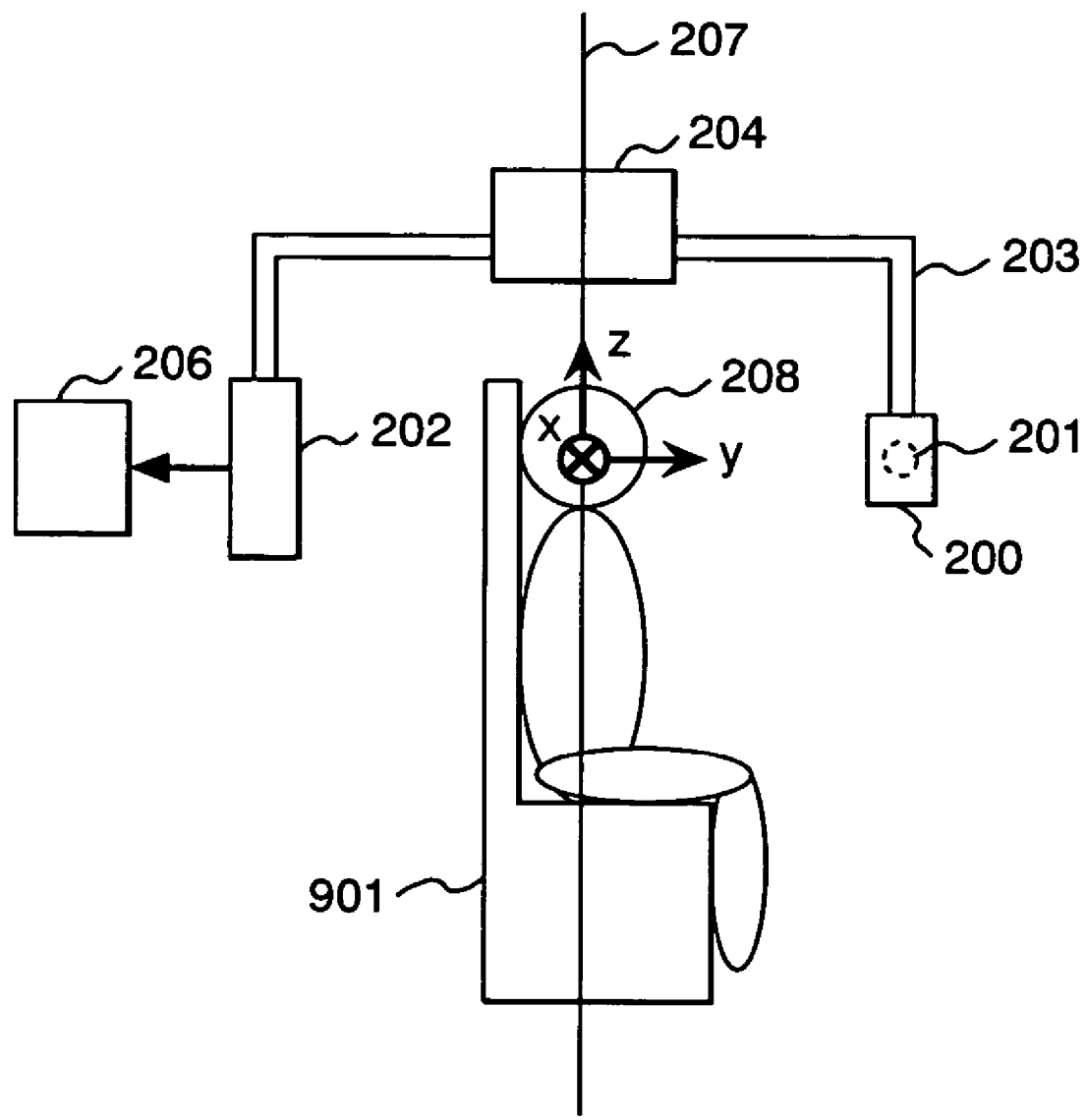
FIG. 9 is a side view exemplarily showing still another structure of an x-ray measuring apparatus according to this invention.

FIG. 9 shows still another structure of an x-ray measuring apparatus according to this invention. A third x-ray measuring apparatus comprises the x-ray source 201 in the x-ray tube 200, the detector 202, the strut 203, the rotating device 204, a chair 901 and the processor 206. The x-ray source 201 and the detector 202 are installed on the strut 203. The strut 203 rotates around the subject 208 sitting on the chair 901 under the control of the rotating device 204. Most commonly, the rotary axis 207 is perpendicular to the floor, and the plane of rotation is parallel to the floor.

The detector 202 may be a flat panel sensor, a combination of an x-ray image intensifier and a CCD camera, an imaging plate, a CCD detector, a solid detector, or the like. Those x-rays generated from the x-ray source 201 pass through the subject 208, converted into electrical signals corresponding to the x-ray intensity by the detector 202, and finally input as measured data into the processor 206. In the processor 206, the measurement data is processed for correction. Specifically, the data is corrected through logarithmic conversion and reconstructed in the form of projection data, thereby obtaining a three-dimensional reconstructed image.

In addition to the logarithmic conversion, a variation in the sensitivity between elements of the detector is corrected, or the geometric distortion is corrected, as needed. Note that the measurement data may be input to the processor 206 in the detector 202, after the measurement data is partially or entirely corrected.

Before executing the reconstructing process, the processor 206 can multiply the projection data by a weight function. The processor 206 has a means for inputting weight functions and storing the input weight functions. In this case, the weight functions are input in the form of profiling or in the form of coefficients of a numerical formula. The means for inputting the weight functions includes inputting using keys on a keyboard or reading from a file, etc. The processor 206 has a mode for inputting the weight functions in the form of an operation menu, and displays an input result on its display during an input operation.

Figure 1:
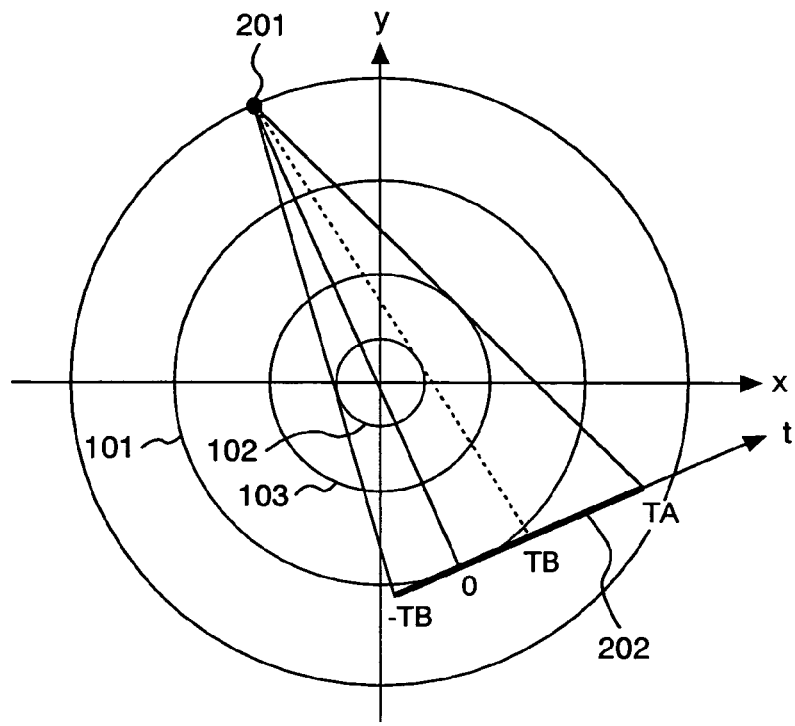
FIG. 1 is a schematic diagram showing the placement of a detector in this invention.

FIG. 1 shows a schematic diagram of the placement of the detector included in the apparatus of this invention. FIG. 1 is a cross-sectional view showing the x-ray measuring apparatus of FIGS. 2, 8 and 9, taken along the plane of rotation. In FIG. 2, the rotary axis 207 is shown horizontally on the illustration space, and the plane of rotation is perpendicular to the rotary axis 207 and to the illustration page. For the sake of explanation, FIG. 2 shows the apparatus in an orthogonal coordinate system wherein the x-axis is taken in the depth direction of the illustration page, the y-axis is taken in the longitudinal direction of the page, and the z-axis is taken in the lateral direction. FIG. 1 shows the x-ray measuring apparatus taken along the planes of the x-axis and y-axis in the illustration of FIG. 2, wherein the z-axis is taken in the depth direction of the page. The detector 202 is placed and shifted a "shift-position" from the front position of the x-ray source 201 in the tangential direction of a rotating track 101. The detector 202 may be in this "shift-position" in the installation, or may be in this "shift-position" after being shifted by a detector shifting means. By setting the detector 202 in the "shift-position", a view of a reconstructed image can be widened in the shifted direction.

Figure 3:
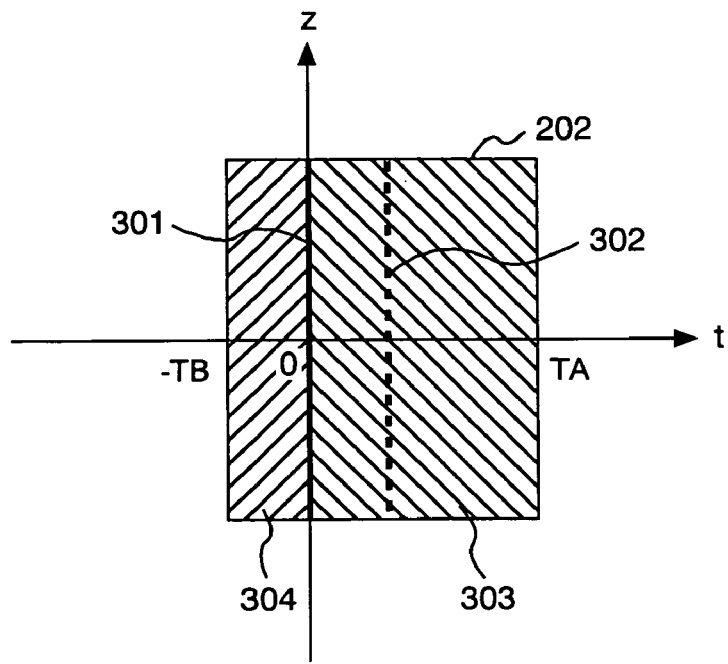
FIG. 3 is a diagram for explaining the detector with a view from an x-ray source.

FIG. 3 shows the detector 202 seen from the x-ray source 201. The illustration shows a rotation center line 301 corresponding to the plane, which is perpendicular to the plane of rotation. This plane includes the x-ray source 201 and the rotation center, and overlaps with the detector 202. The z-axis is taken in a direction parallel to the rotation center line 301 in the detector 202, the t-axis is taken in a direction vertical to the rotation center line 301, and the position of the rotation center line 301 on the t-axis is set as the origin "0". A detector center line 302 is perpendicular to the plane of rotation, and goes along the center of the detector 202. In the case where the detector 202 is placed right in front of the x-ray source 201, the detector center line 302 coincides with the rotation center line 301. In the case where the detector 202 is shifted from the front position of x-ray source 201, the detector center line 302 deviates from the rotation center line 301.

As the detector 202 moves along the t-axis in the positive direction, the detector center line 302 moves along the t-axis in the positive direction. With a reference point of the rotation center line 301, one side of the detector 202 in the forward direction of the movement is referred to as a side 303, while the other side thereof in the backward direction is referred to as a side 304. The distance from the rotation center line 301 to the end of the side 303 is referred to as a distance from the rotation center line 301 to a coordinate TA, while the distance from the rotation center line 301 to the end of the side 304 is referred to as a distance from the rotation center line 301 to a coordinate TB.

The distance from the detector center line 302 to the end of the detector 202 is half the length of the detector 202 along the t-axis direction. In the case where the detector 202 is in the "shift-position", the distance from the rotation center line 301 to the coordinate TA is longer than the distance from the detector center line 302 to the end thereof, while the coordinate TB is shorter than the distance from the detector center line 302 to the end thereof. If the movement distance of the detector 202 is longer than the distance from the detector center line 302 to the end thereof, the detector 202 does not exist around the rotation center line 301, resulting in a loss of projection data and the reconstructed image. If the movement distance of the detector 202 is so controlled as to be shorter than the distance from the detector center line 302 to the end thereof, the loss of projection data can be avoided around the rotation center line 301.

In FIG. 1, if the detector 202 rotates 360 degrees, the projection data can be obtained twice in an area inside a rotating track 102 formed by the locus along a segment enclosed between the x-ray source 201 and the end of the side 304. Specifically, the projection data can be obtained when the x-ray source 201 rotates 0 to 180 degrees and also when the x-ray source 201 rotates 180 degrees to 360 degrees. The projection data can be obtained once in the case where the x-ray source 201 rotates 0 to 360 degrees in an area outside the rotating track 102 formed by the locus along a segment enclosed between the x-ray source 201 and the end of the side 304. This area is inside a rotating track 103 formed by the locus along a segment enclosed between the x-ray source 201 and the end of the side 303. In an area outside the rotating track 103 formed by the locus along a segment enclosed between the x-ray source 201 and the end of the side 303, a loss of projection data occurs in the case where the x-ray source 201 rotates 0 to 360 degrees. That is, the number of projection data pieces contributing to the reconstructing process differs between areas.

Before executing the reconstructing process, a process for multiplying the projection data by a weight is carried out. If the weight is 1.0 for all projection data pieces, a value difference occurs between the rotating tracks 102 and 103, and hence lowering the quantitative characteristics in values of the reconstructed image. This is because the number of projection data pieces contributing to the reconstructing process differs between areas. By multiplying the projection data by a weight corresponding to each projection data piece contributing to the reconstructing process, a reconstructed image satisfying the quantitative characteristics can be obtained without any artifact in the form of a gap between the rotating tracks 102 and 103.

Figure 4:
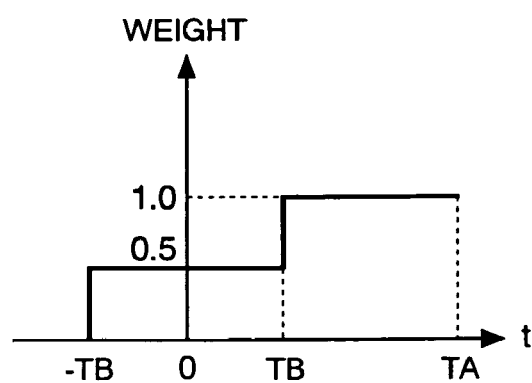
FIG. 4 is a diagram for explaining a profile (1) of a weight function.

FIG. 4 exemplarily shows a profile of a weight function. In the range between coordinates TB and TA, the detector 202 acquires the projection data once during rotation of 360 degrees. In this case, the weight is set 1.0. In the range between a coordinate -TB and the coordinate TB, the detector 202 acquires the projection data twice during rotation of 360 degrees. In this case, the weight is set 0.5. On a coordinate greater than TA and a coordinate smaller than -TB, the detector 202 does not exist, thus the weight is set 0.0.

Figure 5:
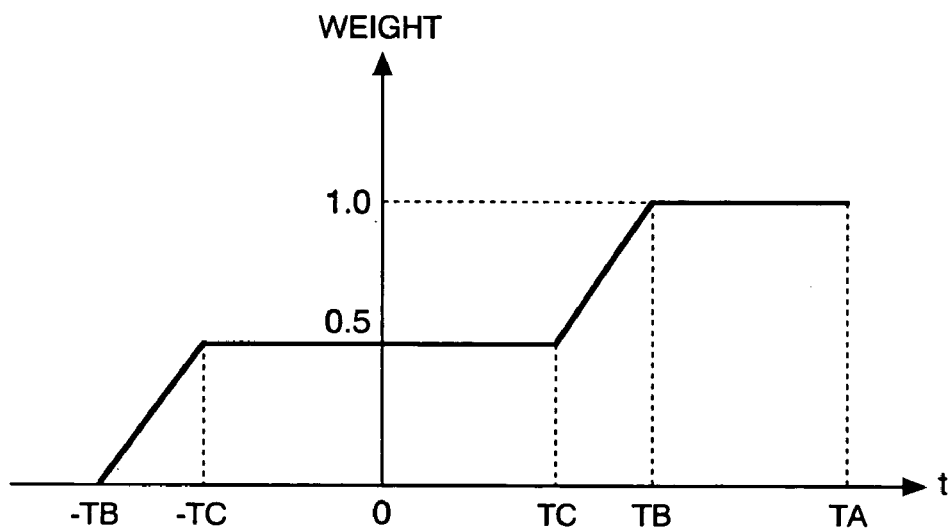
FIG. 5 is a diagram for explaining a profile (2) of a weight function.

FIG. 5 exemplarily shows another profile of a weight function. This weight function is a continuous function. In the range between the coordinates TB and TA, the weight function is set 1.0. On a coordinate greater than TA and a coordinate smaller than -TB, the weight is set 0.0. Arbitrary coordinates TC are equidistant from the rotation center line 301, and the weight is 0.5 in the range between coordinates -TC and TC. The distance from the coordinate TC to the rotation center line 301 is shorter than the distance from the coordinate TB thereto. For example, in the range between the coordinates -TB and -TC, the weight is 0.0 on the coordinate -TB and 0.5 on the coordinate -TC, and expressed in the form of a linear expression. In the range between the coordinate TC and the coordinate TB, the weight is 0.5 on the coordinate TC and 1.0 on the coordinate TB, and expressed in the form of a linear expression.

Figure 6:
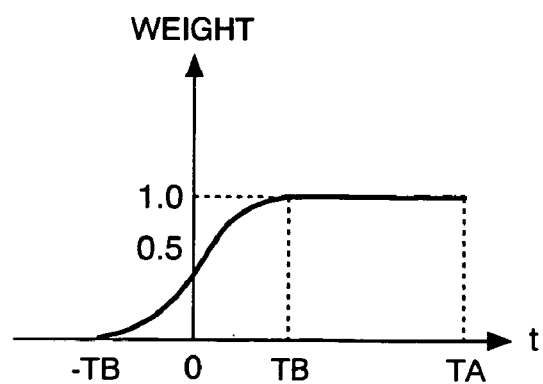
FIG. 6 is a diagram for explaining a profile (3) of a weight function.

FIG. 6 exemplarily shows still another profile of a weight function. This weight function is a continuous function in a differential form. In the range between the coordinates TB and TA, the weight is set 1.0. On a coordinate greater than TA and a coordinate smaller than -TB, the weight is set 0.0. In the range between the coordinate -TB and TB, the weights are so set that the sum of weights becomes 1.0. Those projection data pieces on the coordinates which are equidistant from the rotation center line 301 contribute to the same pixel of the reconstructed image. Hence, the profile of the weight function is 0.5 in the position of the rotation center line 301 in a point symmetrical shape with a center about the position of the rotation center line 301. For example, the weight function is a sin function with an axial center about the position of the rotation center line 301.

Figure 7:
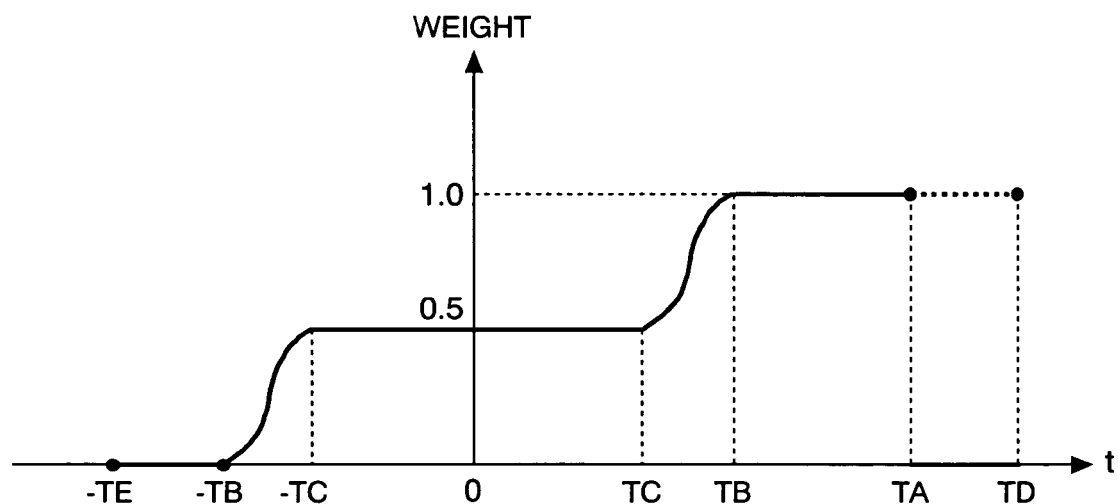
FIG. 7 is a diagram for explaining a profile (4) of a weight function.

FIG. 7 shows yet another profile of a weight function. In the range between the coordinates TB and TA, the weight is set 1.0. On a coordinate greater than TA and a coordinate smaller than -TB, the weight is set 0.0. Arbitrary coordinates TC are equidistant from the rotation center line 301, and the weight is 0.5 in the range between coordinates -TC and TC. The distance from the rotation center line 301 to TC is shorter than the distance from the rotation center line 301 to TB. In the range between the coordinates -TB and -TC and the range between coordinate TC and TB, the weight function is so set that the sum of weight functions on the coordinates which are equidistant apart from the rotation center line 301 is 1.0. In the range between the coordinates -TB and -TC and the range between TC and TB, a function having a differential function in a continuous form is set as a weight function. Such a function in a continuous form may, for example, be a sin function with an axial center about the center line of -TB and -TC, or a sin function with an axial center about the center line of TC and TB.

The weight function shown in FIG. 7 has the following advantages as compared to the weight function shown in FIG. 6. Using the weight function of FIG. 6, in the case where the detector 202 is in the "shift-position", a problem is that noise increases in the central part of the view of the reconstructed image. This problem is particularly obvious as compared to the case where the detector 202 is placed in the "central position", i.e. in front of the x-ray source 201, even if the projection data is obtained from the opposing direction. In the case of "central position", an equal weight is given to opposing data, thereby leveling two pieces of opposing data. As a result of this, noise of the reconstructed image can be reduced to $1/\sqrt{2}$. On the contrary, using the weight function of FIG. 6, the weights of the opposing data are so leveled so as to be 1.0 in total. Thus, the noise in the reconstructed image is greater than the value in simple leveling in the case of the "central position". Therefore, using the weight function of FIG. 6, the noise increases more than the case of the "central position", even in the central part where the projection data is obtained from the opposing direction. Using the weight functions of FIG. 7, such a problem can be settled. In FIG. 7, the weights of the opposing data pieces are all 0.5 in the center part of the view. This corresponds to the weights in the case of simple leveling in the "central position", thus obtaining the same preferable noise characteristics as the case of the "central position". In this manner, using the weight functions of FIG. 7, in the reconstructing in the small field of view, the same weight (all 0.5) as that in the "central position" can be applied. Thus, during the "shift-position", processing can be executed both in "large field imaging (weight in the "shift-position")" and in the "small field-of-view reconstructing" having the same noise characteristics as that in the "central position". That is, without a laterally moving mechanism of a flat panel sensor which moves in accordance with the variable field of view, a system including both a "small field-of-view imaging system" with the same weight and a "large field-of-view shift-position weight imaging system" can be realized.

Figure 10:
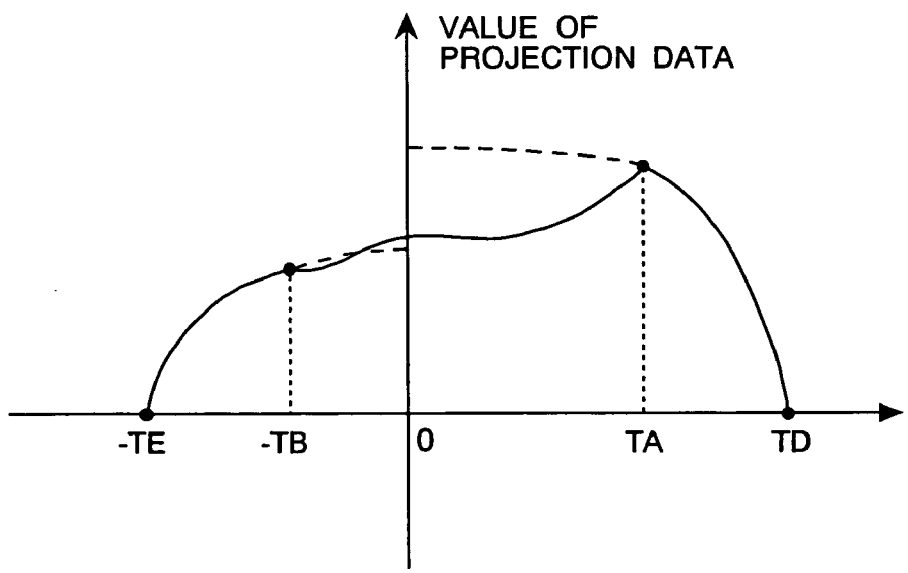
FIG. 10 is a diagram exemplarily showing a profile of estimated projection data.
Figure 11:
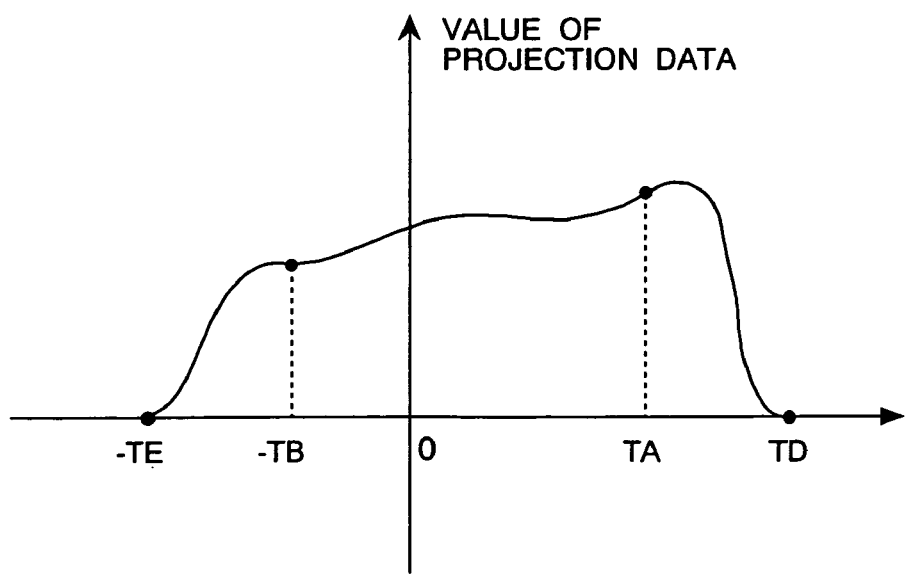
FIG. 11 is a diagram exemplarily showing another profile of estimated projection data.

If there is no restriction in the detectable area of the detector 202, the projection data has a value even on a coordinate greater than TA or a coordinate smaller than -TB. To improve the quantitative characteristics in values of the reconstructed image, projection data corresponding to a coordinate greater than TA and a coordinate smaller than -TB is estimated and applied for the reconstructing process. For example, as shown in FIG. 10, when to estimate the projection data by a coordinate TD, a profile of the estimated projection shows an elliptic function with an axial center about the rotation center line 301. This elliptic function maps the same value as the projection data measured on the coordinate TA and shows "0" on the coordinate TD. In the case where to estimate the projection data by a coordinate -TE, a profile of the estimated projection data shows an elliptic function with an axial center about the rotation center line 301. This elliptic function maps the same value as the projection data measured on the coordinate -TB and shows "0" on a coordinate -TE. In another example, as illustrated in FIG. 11, a profile of estimated projection data shows a function. This function maps the same value as the projection data measured on the coordinate TA, has the same slope as that of the projection data measured near the coordinate TA, and shows "0" on the coordinate TD. Further function maps the same value as the projection data measured on the coordinate -TB, has the same slope as the projection data measured near the coordinate -TB, and shows "0" on the coordinate -TE. In this case, the above weight function maps 1.0, as shown with a dotted line in FIG. 7, from the coordinate TA to the coordinate TD, and maps 0.0 from the coordinate -TB to the coordinate -TE.

In the above embodiment, the explanations were made to the case where the x-ray source 201 and the detector 202 rotate 360 degrees, and the projection data is obtained twice in an area in the rotating track 102 along the segment enclosed between the x-ray source 201 and the end of the side 304. Inside the rotating track 102, if the rotation was so made at an angle that the projection data was obtained once, the weight is obtained by multiplying the above value by 2.0, thereby achieving the same effect as the above.

In the above embodiment, a process for multiplying the projection data after being logarithmic converted by the weight is carried out. In another embodiment, data before being logarithmic converted can be multiplied by an exponentially converted weight, thereafter logarithmic converting the data. In such a case, the processor 206 executes an exponentially converting process for the weight value, multiplies the measurement data by the exponentially converted weight, executes a logarithmic converting process for the data multiplied by the weight, and then executes a reconstructing process using the data after being logarithmic converted. Alternatively, when inputting the weight to the processor, the weight after being exponentially converted can be input. Further, the exponentially converting process is executed for the input weight, and then the weight can be stored in the processor 206. In this case, the processor 206 multiplies the measurement data by the exponentially converted weight, the data after being multiplied by the weight is logarithmic converted, thereafter executing the reconstructing process using the logarithmic converted data.

As explained above, according to the present invention, the x-ray detector is shifted by a distance shorter than half the length of the x-ray detector along the plane of rotation, in the tangential direction of the plane of rotation generated by the x-ray tube. In this placement, the processor executes a process for obtaining projection data by logarithmic converting measurement data, a process for multiplying the obtained projection data by a weight, and a process for obtaining reconstructed data by executing a reconstructing process using the data after being multiplied by the weight, thereby acquiring a three-dimensional reconstructed image. Above all, it is possible to extend the field of view of a reconstructed image in a direction parallel to the plane of rotation and to obtain a reconstructed image without any artifact in the center of the rotation.

According to the present invention, the x-ray detector is shifted by a distance shorter than half the length of the x-ray detector along the plane of rotation, in the tangential direction of the plane of rotation generated by the x-ray tube. In this placement, the processor executes a process for multiplying the value of measurement data by an exponentially converted weight, a process for obtaining projection data by logarithmic converting the data multiplied by the weight, and a process for obtaining reconstructed data by executing a reconstructed data using the projection data. Above all, it is possible to extend the field of view of a reconstructed image in a direction parallel to the plane of rotation and to obtain a reconstructed image without any artifact in the center of the rotation.

According to the present invention, because the detector is a one-dimensional detector, it is possible to realize a CT apparatus that can extend the field of view of a reconstructed image in a direction parallel to the plane of rotation, and can obtain a reconstructed image without any artifact in the center of the rotation.

According to the present invention, because the detector is a two-dimensional detector, it is possible to realize a cone-beam CT apparatus that can extend the field of view of a reconstructed image in a direction parallel to the plane of rotation, and can obtain a reconstructed image without any artifact in the center of the rotation.

According to the present invention, the rotation center line corresponding to the axis of rotation is set on the measurement data, and the distance between the rotation center line and the end of the measurement data is measured. Further, a boundary line is set in a predetermined position along the longer distance from the rotation center line to the end of the detector. This predetermined position and the end of the shorter distance of the detector are equidistant apart from the rotation center line. The weight in the range from the boundary line to the end of the longer distance is 1.0, the weight at the rotation center line is 0.5, and the weight in the range from the rotation center line to the end of the shorter distance is 0.0. By this setting, the quantitative characteristics in the value of the extended reconstructed image can be improved.

According to the present invention, a function representing the weight is a continuous function. The sum of those weights in positions equidistant apart from the rotation center line is set 1.0, thereby reducing the artifact in the extended reconstructed image.

According to the present invention, the differential form of the weight function is a continuous function, thereby reducing the artifact with high accuracy in the extended reconstructed image.

According to the present invention, the profile of the weight is in a point symmetrical shape with a center about the intersection with the rotation center line, thereby improving the quantitative characteristics in the value of the extended reconstructed image.

What is claimed is:

1. An x-ray measuring apparatus comprising:
    an x-ray source for generating x-rays to be emitted to a subject;
    an x-ray detector which detects measurement data regarding said subject;
    a rotating device which changes a relative position of said x-ray source and said x-ray detector with respect to said subject;
    a processor which executes an arithmetic operation for said measurement data; and
    a detector shifting means for shifting said x-ray detector, wherein
    said x-ray detector which is a one-dimensional detector or a two-dimensional detector, is placed and shifted by a distance shorter than half of length of said x-ray detector along a line parallel to plane of rotation from front position of said x-ray source, in a tangential direction of the plane where said x-ray source rotates, and
    said processor executes a process for obtaining projection data by logarithmically converting said measurement data,
    a process for multiplying a value of said projection data by a weight, and
    a process for obtaining reconstructed data by executing a reconstructing process using said data after being multiplied by the weight, thereby obtaining a three-dimensional reconstructed image, and
    wherein, in said process for multiplying the weight,
    a rotation center line corresponding to axis of rotation is set on said measurement data,
    a distance from said rotation center line to an end of said measurement data is measured, and a boundary line is set in a position along a longer distance from the rotation center line being equidistant between said position and end of a shorter distance, and
    a weight from said boundary line to an end of the longer distance is set 1.0, a weight at said rotation center line is set 0.5, and a weight at the end of the shorter distance is set 0.0.

2. The x-ray measuring apparatus according to claim 1, wherein
    a function expressing said weight is a continuous function in said process for multiplying the weight, and
    sum of weights in positions which are equidistant apart from said rotation center line is 1.0.

3. An x-ray measuring apparatus comprising:
    an x-ray source for generating x-rays to be emitted to a subject;
    an x-ray detector which detects measurement data regarding said subject;
    a rotating device which changes a relative position of said x-ray source and said x-ray detector with respect to said subject;
    a processor which executes an arithmetic operation for said measurement data: and
    a detector shifting means for shifting said x-ray detector, wherein said x-ray detector which is a one-dimensional detector or a two-dimensional detector, is placed and shifted by a distance shorter than half of length of said x-ray detector along a line parallel to plane of rotation from front position of said x-ray source, in a tangential direction of the plane where said x-ray source rotates; and said processor executes a process for obtaining projection data by logarithmically converting said measurement data, a process for multiplying a value of said projection data by a weight, and a process for obtaining reconstructed data by executing a reconstructing process using said data after being multiplied by the weight, thereby obtaining a three-dimensional reconstructed image, and wherein, in said process for multiplying the weight, a rotation center line corresponding to axis of rotation is set on said measurement data in said process for multiplying the weight, first boundary lines are set in positions which are equidistant apart from said rotation center line, second boundary lines are set in positions which are equidistant apart from said rotation center line, externally from said first boundary lines, weights from one of said first boundary lines to an other side over said rotation center line are set 0.5, a continuous function of a weight from said one boundary line to one of said second boundary line, which are on a same side with respect to said rotation center line, maps 0.5 to 0.0 in a changing manner, a continuous function of a weight from the other side of said first boundary line to an other side of said second boundary line, which are on a same side with respect to said rotation center line, maps 0.5 to 1.0 in a changing manner, and a weight from the other side of said second boundary line to an end of said measurement data on a same side with respect to said rotation center line, is set 1.0.

4. The x-ray measuring apparatus according to claim 3, wherein, in said process for obtaining the reconstructed data, a reconstructing process is executed using projection data of an arbitrary range, of a range from said one first boundary line to the other side of boundary line.

5. An x-ray measuring apparatus comprising:

an x-ray source for generating x-rays to be emitted to a subject;

an x-ray detector which detects measurement data regarding said subject;

a rotating device which changes a relative position of said x-ray source and said x-ray detector with respect to said subject;

a processor which executes an arithmetic operation for said measurement data; and a detector shifting means for shifting said x-ray detector, wherein said x-ray detector which is a one-dimensional detector or a two-dimensional detector, is placed and shifted by a distance shorter than half of length of said x-ray detector along a line parallel to plane of rotation from front position of said x-ray source, in a tangential direction of the plane where said x-ray source rotates, and said processor executes a process for multiplying a value of said measurement data by an exponentially converted value of a weight, a process for obtaining projection data by executing a logarithmic converting process for said measurement data after being multiplied by the exponentially converted value of a weight, and a process for obtaining reconstructed data by executing a reconstructing process using said projection data, thereby obtaining a three-dimensional reconstructed image, and wherein, in said process for multiplying the weight, a rotation center line corresponding to axis of rotation is set on said measurement data, a distance from said rotation center line to an end of said measurement data is measured, and a boundary line is set in a position along a longer distance from the rotation center line being equidistant between said position and end of a shorter distance, and a weight from said boundary line to an end of the longer distance is set 1.0, a weight at said rotation center line is set 0.5, and a weight at the end of the shorter distance is set 0.0.

6. The x-ray measuring apparatus according to claim 5, wherein a function expressing said weight is a continuous function in said process for multiplying the weight, and sum of weights in positions which are equidistant apart from said rotation center line is 1.0.

7. An x-ray measuring apparatus comprising:

an x-ray source for generating x-rays to be emitted to a subject;

an x-ray detector which detects measurement data regarding said subject;

a rotating device which changes a relative position of said x-ray source and said x-ray detector with respect to said subject;

a processor which executed an arithmetic operation for said measurement data; and a detector shifting means for shifting said x-ray detector, wherein said x-ray detector which is a one-dimensional detector or a two-dimensional detector, is placed and shifted by a distance shorter than half of length of said x-ray detector along a line parallel to plane of rotation from front position of aid x-ray source, in a tangential direction of the plane where said x-ray source, in a tangential direction of the plane where said x-ray source rotates, and said processor executes a process for multiplying a value of said measurement data by an exponentially converted value of a weight, a process for obtaining projection data by executing a logarithmic converting process using said projection data, thereby obtaining a three-dimensional reconstructed image, and wherein, in said process for multiplying the weight, a rotation center line corresponding to axis of rotation is set on said measurement data in said process for multiplying the weight, first boundary lines are set in positions which are equidistant apart from said rotation center line, second boundary lines are set in positions which are equidistant apart from said rotation center line, externally from said first boundary lines, weights from one of said first boundary lines to an other side over said rotation center line are set 0.5, a continuous function of a weight from said one boundary line to one of said second boundary line, which are on a same side with respect to said rotation center line, maps 0.5 to 0.0 in a changing manner, a continuous function of a weight from the other side of said first boundary line to an other side of said second boundary line, which are on a same side with respect to said rotation center line, maps 0.5 to 1.0 in a changing manner, and a weight from the other side of said second boundary line to an end of said measurement data on a same side with respect to said rotation center line, is set 1.0.

8. The x-ray measuring apparatus according to claim 7, wherein, in said process for obtaining the reconstructed data, a reconstructing process is executed using projection data of an arbitrary range, of a range from said one first boundary line to the other side of boundary line.

* * * * *